(12) United States Patent
Erling et al.

(10) Patent No.: US 9,885,700 B2
(45) Date of Patent: Feb. 6, 2018

(54) METHOD AND APPARATUS FOR DETECTING ELUTION OF SAMPLES

(71) Applicant: Wallac Oy, Turku (FI)

(72) Inventors: Ida Erling, Turku (FI); Raimo Harju, Turku (FI)

(73) Assignee: Wallac Oy, Turku (FI)

( * ) Notice: Subject to any disclaimer, the term of this patent is extended or adjusted under 35 U.S.C. 154(b) by 0 days.

(21) Appl. No.: 15/076,782

(22) Filed: Mar. 22, 2016

(65) Prior Publication Data
US 2016/0202238 A1 Jul. 14, 2016

Related U.S. Application Data

(62) Division of application No. 12/937,543, filed as application No. PCT/FI2009/050788 on Oct. 1, 2009, now Pat. No. 9,329,120.

(30) Foreign Application Priority Data

Oct. 3, 2008 (FI) ...................................... 20085934

(51) Int. Cl.
| | | |
|---|---|---|
| *G01N 21/25* | (2006.01) | |
| *G01N 33/49* | (2006.01) | |
| *B01L 3/00* | (2006.01) | |
| *G01N 21/31* | (2006.01) | |

(52) U.S. Cl.
CPC ............ *G01N 33/49* (2013.01); *B01L 3/5085* (2013.01); *G01N 21/253* (2013.01); *G01N 21/31* (2013.01); *B01L 2300/0654* (2013.01); *B01L 2300/0681* (2013.01)

(58) Field of Classification Search
None
See application file for complete search history.

(56) References Cited

U.S. PATENT DOCUMENTS

| | | | |
|---|---|---|---|
| 5,204,267 A | 4/1993 | Jangbir et al. | |
| 5,273,718 A | 12/1993 | Sköld et al. | |
| 5,638,170 A | 6/1997 | Trinka et al. | |
| 5,641,682 A | 6/1997 | Pagels et al. | |
| 6,187,531 B1 | 2/2001 | Tyrrell | |
| 6,825,921 B1 * | 11/2004 | Modlin ................ | G01N 21/255 235/454 |
| 2005/0208510 A1 * | 9/2005 | Latham .............. | C12N 15/1006 435/6.12 |

FOREIGN PATENT DOCUMENTS

| | | |
|---|---|---|
| JP | 1124749 A | 5/1989 |
| WO | WO 0028089 | 5/2000 |
| WO | WO 03052390 | 6/2003 |

OTHER PUBLICATIONS

Database WPI Week 193926 Thomson Scientific, London, GB; AN 1989-187511 XP002562137-JP 01124749 (Fujimura A).
Reclos, G. J. et al. "G-6-PD Diagnosis: Modification of the standard method eliminates the need for an additional Hemoglobin determination" Retrieved on Jul. 8, 2009 from http://web.archive.org/web/20071016201920/http://www.rddiagnostics.com/RDD%20method%20paper.doc Publically available on Oct. 16, 2007.

* cited by examiner

*Primary Examiner* — Christopher M Gross
(74) *Attorney, Agent, or Firm* — Seppo Laine Oy

(57) ABSTRACT

The invention relates to a method and apparatus for detecting elution of a sample from a sample substrate to incubation buffer contained in a sample well while the sample substrate is still within the well. The method comprises measuring light absorption of the contents of the sample well at a predefined wavelength or wavelength range, and determining, based on the absorption measurement, the degree of elution of the sample. According to the invention, a wavelength or wavelength range is used which is absorbed by at least one elutable component of the sample but transmitted by the sample substrate. The invention provides a reliable way of determining the degree of elution of blood samples in neonatal screening, for example.

6 Claims, 3 Drawing Sheets

METHOD AND APPARATUS FOR DETECTING ELUTION OF SAMPLES

FIELD OF THE INVENTION

The invention relates to a method and apparatus of handling samples of body fluids, such as blood. In particular, the invention relates to assays and to instruments where the samples are small disks punched out of dried blood spots on carrier material like filter paper (Guthrie card) or other fibrous substrate and transferred into sample containers like into wells of microtiter plate

RELATED ART

Sample analyses of the above kind are frequently carried out using microtiter plates, the wells of which contain a piece of sample-containing substrates. An example of such analysis is blood screening of neonates. Such analysis comprises collecting of blood samples from neonates by impregnating blood samples to certain areas of fibrous cards (substrates) so as to form sample spots on the cards. The samples are let to dry onto the cards. Typically the cards are sent by mail into the central laboratory where the cards are fed to a manual or automatic card handling apparatus, which punches one ore more small-diameter sample disks, from each of the sample spots. The sample disks may be of a diameter of a few millimeters depending on the amount of the sample needed for the analyte test and also the size of elution container for example, if microtiter plate well, diameter of 3.2 mm. The disks are conveyed to wells of the microtiter plate so that one sample well includes typically exactly one disk. The wells are then subjected to different (bio)chemical preparation steps depending on the chemistry applied. Thereafter the amount of analyte(s) in the wells is measured, for example fluorometrically. In a typical assay, the sample disks are first submerged in a suitable incubation buffer within the wells in order to elute (e.g. extract or dissolve) analyte from the disk to the buffer. The amount of the analyte can further be detected for example optically, i.e. using fluorescence, time-resolved fluorescence, absorbance or luminescence measurements or using radioactive labeling or mass spectroscopy It is crucial to the analysis that each well contains a sample disk, which is correctly punched from fibrous substrate card and the impregnated sample from the disk is totally extracted into the buffer Otherwise the analysis of the sample is not reliable.

However, it sometimes may happen that not all wells are containing a sample disk for various reasons. Possibly the disk is not successfully punched in a puncher, the disk is lost in the puncher or during transport of the plate from the puncher to the analysis apparatus, or the disk is lost within the analysis apparatus. In particular, fibrous disks are prone to static electricity (see e.g. U.S. Pat. No. 5,638,170) accumulated during punching or later, which increases the risk of losing a disk. On the other hand, a sample disk may not contain enough blood due to erroneous punching, or stick to the upper portion of well walls, in which cases elution of the sample also cannot take place.

Traditionally, an operator of the analysis apparatus checks that there is a disk in each well by visual inspection before placing the plate into the apparatus or after the measurement again depending on the type of chemistry used. This is however time-consuming and susceptible to human errors. Afterward detection is not always possible if a disk-remover unit is used. In addition, losing a disk within the apparatus or improper elution of the sample, even if a well contains a disk can not be detected by visual inspection.

WO 03/052390 and WO 00/28069 disclose methods for analysis of blood samples from dried blood spot samples eluted from blood disks. Before analysis, a sample of the eluant is transferred from the elution container to another container to avoid blocking of light path by the sample disk present in the elution container. However, for the simplicity and reliability of the process, analysis from a container still having the disk therein would be preferable.

AutoDelfia system from PerkinElmer is has means for controlling the success of elution. This instrument is equipped only with time-resolved fluorescence detection and to detect missing spots it uses a modified protocol of time-resolved measurement immediately after elution and before removing the disk. From these measurements one can evaluate probability of unsuccessful elution but the procedure used is complicated and sets up some expectations for plate maps and possible number of missing disks. Although the method finds all missing spots, it also produces false alerts, which means extra costs and time delays for screening.

SUMMARY OF THE INVENTION

It is an aim of the invention to find a simple and reliable method for automatically verifying successful elution while the sample disk or the like substrate is within the elution well, thus ensuring safe analysis of blood samples and also avoiding extra testing due to false alerts.

Furthermore, it is an aim of the invention to achieve an elution control method which can be used irrespective of whether the substrate is floating on or submerged within the incubation buffer contained in the well.

The aims of the invention are achieved by the method and apparatus as defined in the independent claims. Thus, it has been found that automatic detection of elution can be carried out by directing light to a sample well at a wavelength or wavelength range which is absorbed by at least one elutable component of the sample but at least partly transmitted by the sample substrate (i.e. the sample disk). The calculated absorbance value of the amount of light transmitted through the well and further detected by a detector, is indicative of the degree of real elution irrespective of the position or presence of the sample disk in the well.

Advantageous embodiments of the invention are the subject of dependent claims.

In particular, it has been found that fibrous sample substrates, such as sorbent papers or the like, have a sufficient optical transmission around the absorption peak of haemoglobin, that is, approximately 420 nm. On the other hand, haemoglobin is easily eluted from blood samples and thus serves as a good indicator of the degree of their elution.

According to one embodiment, the sample disk is present in the sample well during analyte detection. This is crucial if the screening assay is such that the disk is not removed from the sample well in a separate disk removal step before the measurement of the analyte. An example of an assay which can be carried out without removing the disk is the GALT assay widely used in screening newborn babies.

According to one embodiment the eluted sample is transferred into another plate without transferring the disks. Here the present invention is exploited to verify that the transferred sample is valid by absorption measurement.

According to one embodiment, the elution detection according to the invention is performed automatically in parallel or successive manner for a plurality of sample wells in an optical sample measurement apparatus. In particular, the detection provides significant advantages in connection with high-throughput screening using a plurality of stored (e.g. stacked) microtiter plates each containing an array of samples, as the risk of obtaining false screening results due to human errors or losing of disks within the screening apparatus or incomplete elution of samples is practically avoided.

According to one embodiment, the present invention concerns an apparatus for optical analysis of samples eluted from a sample disk to incubation buffer contained in a sample well of a sample holder loadable into the apparatus. The apparatus includes
- a light source for emitting light through the sample well at a predefined wavelength or wavelength range absorbed by at least one elutable component of the sample but transmitted by the sample disk,
- a detector for detecting light transmitted through the well,
- a computing or control unit adapted to determine, based on the light detected, the degree of elution of the sample in the sample well.

In addition, the apparatus typically includes
- a storage unit for a plurality of microtiter plates serving as said sample holder, and
- an optical measurement unit adapted for the measurement the amount of predefined analyte in the eluted sample.

The light source and detector used in determining the degree of elution of the sample are used also by said optical measurement unit for the measurement of the amount of the analyte. Accordingly, no separate units are required reducing manufacturing costs and processing times. Preferably, the degree of elution of the sample is adapted to be determined using the optical measurement unit before or after the optical measurement of the analyte in each sample well. If the actual analyte measurement is performed e.g. fluorometrically the analyzator could be easily equipped with a simple filter photometer for absorbance measurement.

The invention offers advantages over the art, especially by eliminating/controlling the effect of the presence or position of the disk on the signal measured, and thus being able to determine the degree of real elution. Along the invention the use of absorption measurement or the like in the instrument gives a clear and absolute signal from every sample alone without any complicated data analysis. Furthermore, it does not need any special plate map or any minimum number of wells or history data. The measured signal is a direct criterion for the quality of the test. In other words, a threshold absorbance value below which the proper elution can be assumed not to have taken place can be reliably determined in all possible situations that may occur in the well (e.g. disk floating, disk submerged, disk stuck to the a wall, disk tilted, disk removed from the well).

As defined herein, "incubation buffer" is a solution typically comprising analyte specific reagents such as substrates, cofactors, label molecules, antibodies, enzymes, and buffer components.

Further embodiments and advantages of the invention are explained in the detailed description with reference to the attached drawings.

DETAILED DESCRIPTION OF EMBODIMENTS

The present invention can be used for automatically detecting whether a blood disk currently is or has been in a well of the microtiter plate. This is achieved by measuring the absorbance of light in the well at a suitable wavelength absorbed by haemoglobin eluted from the blood disk to buffer within the well.

Figure 1:
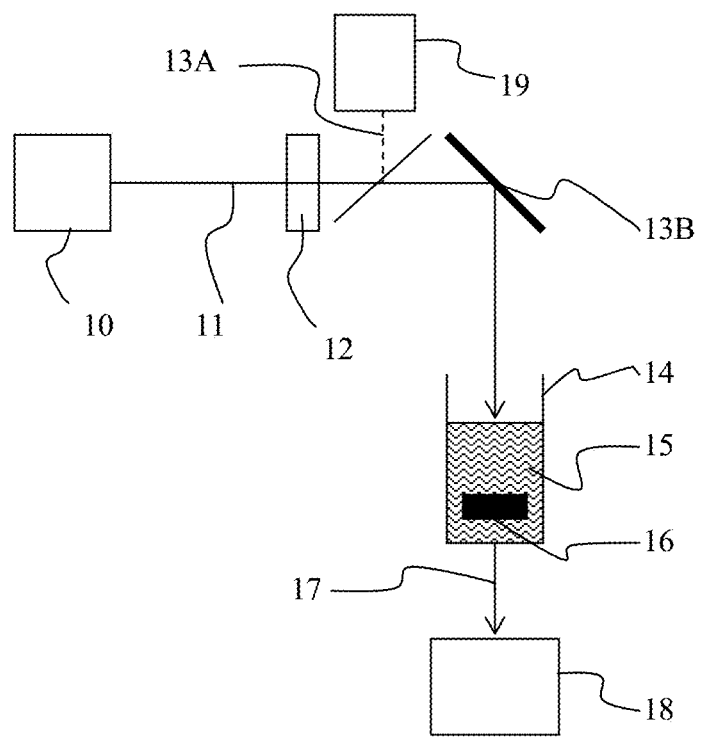
FIG. 1 shows a measurement setup for elution detection according to one embodiment of the invention.

The general principle of the elution detection is illustrated in FIG. 1. Light 11 is emitted by a light source 10 through an optical filter 12 which is adapted to limit the wavelength band to the desired range, for example, around 420 nm. The small portion of the light 11 is directed to the reference detector via a partial reflector 13A. The remaining light is further directed via mirror 13B to the sample well 14 from above. Overall there are used lenses to collect light from the light source and to focus it in to the sample. The lenses are not shown on the figure. The well 14 is typically part of a well array of a microtiter plate. The well 14 contains incubation buffer 15 and a sample disk 16. In the figure, the disk 16 is shown submerged position. Transmitted light 17 is collected and focused to the detector 18 using the lens system.

Absorption measurement could be performed by many different ways. In addition to the embodiment disclosed in FIG. 1, the light source and the detector can be located below and above the sample, respectively. In the case of single containers, in turn, the absorbance can be measured through side walls of the container.

If a well based on the measurement is detected as not containing a well-eluted sample, the actual measurement of the analyte may be skipped or the measurement results may be disregarded in respect of such well.

The threshold signal strength may be individually determined for each assay or series of assays based on the real patient data or it may be pre-programmed to the apparatus based on prior experiments or calculations, for example. Examples 1-3 later in this document clarify the efficiency of the invention.

The following measurement examples illustrate the efficiency of the invention in practice. In the measurements, different analytes of blood samples impregnated to sorbent sample disks were measured by absorbance of the wavelength of 420 nm. Haematocrite values of 0.3, 0.4, 0.5 and 0.6 were used, corresponding to haemoglobin values of 9.6 g/dl, 12.3 g/dl, 16.1 g/dl and 19.0 g/dl. (The lower limit for the haemoglobin values of 3-day old neonatals is 14.6-15.6 g/dl). The two lowest haematocrite values were measured both when the disk is in the well and when the disk was removed from the well. In addition, wells with white disks (i.e. disks not containing an impregnated sample), wells containing only buffer and empty wells were measured. In the case of GALT (example 3), additional samples (calibrators A-F and controls N and AbN prepared from sheep blood) were measured.

Figure 2A:
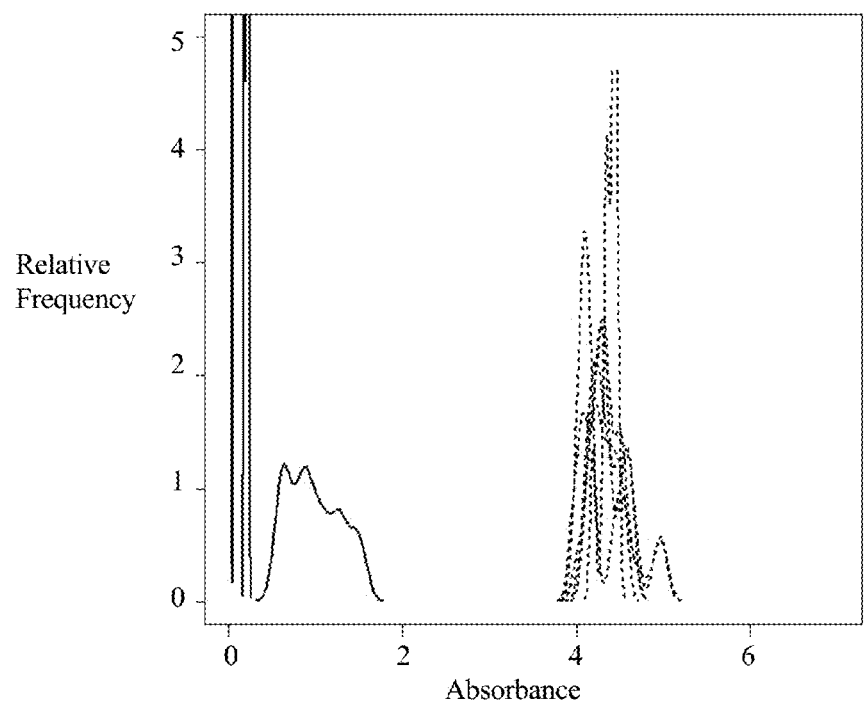
FIGS. 2A-2C show graphically results of experiments carried out using the invention.
Figure 2B:
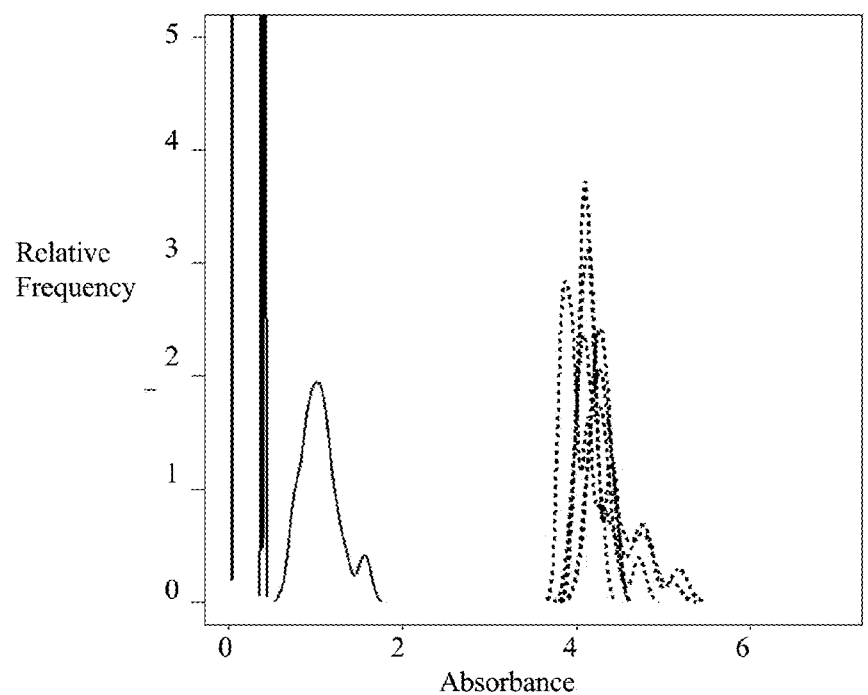
Figure 2C:
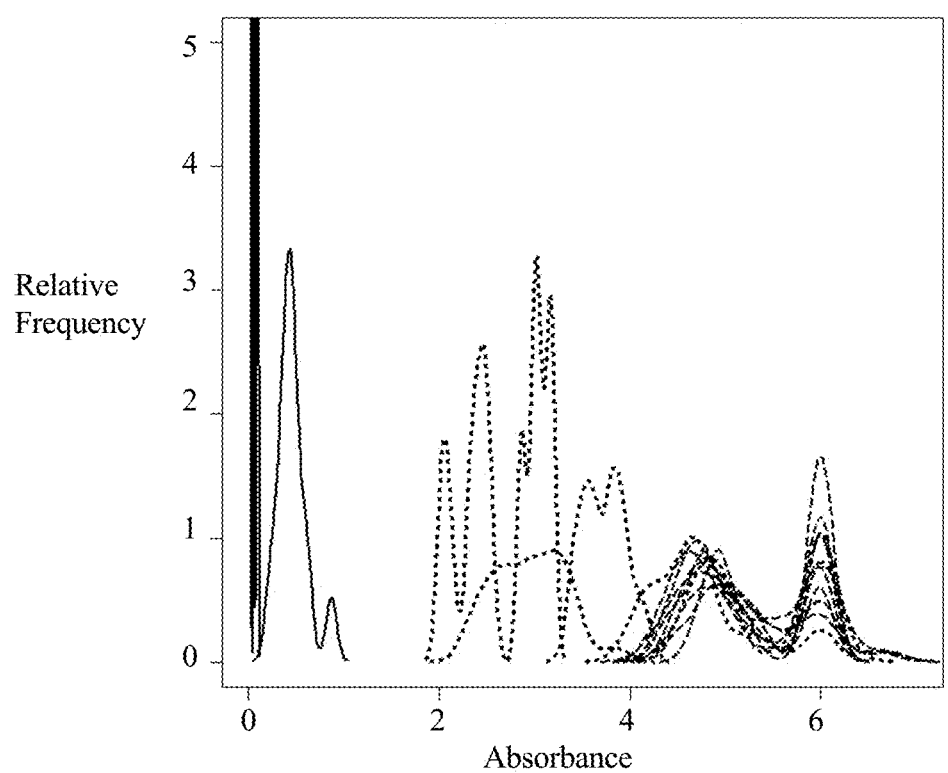

The results of the measurements are shown in Tables 1-3 and FIGS. 2A-2C. The Figures shows graphs of absorbance values and their relative frequencies of incidence and for each sample type (the integral area of each curve amount to 1). Samples with no blood, that is, the three undesired well conditions (white disks, no disks and empty wells) are drawn with solid lines and blood samples are drawn with dotted lines. As can be seen, in each case the three undesired conditions could be reliably distinguished from the cases where the wells contained a real blood sample (by selecting a threshold absorbance signal at the gap between the two groups of measurements.

Example 1 (TSH Analyte)

TABLE 1

Mean, standard deviation, minimum, maximum and number of samples of absorbance measurement of TSH-analyte for different sample types.

| Sample | n | Mean | STD | Max | Min |
|---|---|---|---|---|---|
| Hkr[a] 0.3 | 27 | 4.33 | 0.16 | 4.67 | 4.00 |
| Hkr 0.3, disk removed | 9 | 4.24 | 0.23 | 4.59 | 4.02 |
| Hkr 0.4 | 27 | 4.24 | 0.17 | 4.55 | 3.94 |
| Hkr 0.4 disk removed | 9 | 4.38 | 0.09 | 4.46 | 4.19 |
| Hkr 0.5 | 27 | 4.44 | 0.25 | 4.98 | 4.14 |
| Hkr 0.6 | 27 | 4.40 | 0.26 | 5.00 | 4.10 |
| White disk | 27 | 0.98 | 0.30 | 1.54 | 0.56 |
| No disk | 27 | 0.20 | 0.02 | 0.24 | 0.17 |
| Empty well | 27 | 0.04 | 0.00 | 0.05 | 0.03 |

[a]Hkr = haematocrite

Example 2 (nT4 Analyte)

TABLE 2

Mean, standard deviation, minimum, maximum and number of samples of the absorbance measurement of nT4-analyte for different sample types.

| Sample | n | Mean | STD | Max | Min |
|---|---|---|---|---|---|
| Hkr 0.3 | 27 | 4.15 | 0.13 | 4.48 | 3.94 |
| Hkr 0.3, disk removed | 9 | 3.99 | 0.16 | 4.28 | 3.83 |
| Hkr 0.4 | 27 | 4.20 | 0.20 | 4.75 | 3.94 |
| Hkr 0.4, disk removed | 9 | 4.18 | 0.15 | 4.45 | 3.99 |
| Hkr 0.5 | 27 | 4.41 | 0.26 | 5.11 | 4.08 |
| Hkr 0.6 | 27 | 4.44 | 0.30 | 5.20 | 4.10 |
| White disk | 27 | 1.05 | 0.22 | 1.56 | 0.73 |
| No disk | 27 | 0.40 | 0.02 | 0.43 | 0.37 |
| Empty well | 27 | 0.04 | 0.00 | 0.05 | 0.04 |

Example 3 (GALT Analyte)

TABLE 3

Mean, standard deviation, minimum, maximum and number of samples of the absorbance measurement of GALT-analyte for different sample types.

| Sample | n | Mean | STD | Max | Min |
|---|---|---|---|---|---|
| A calibrator | 27 | 5.25 | 0.63 | 6.00 | 4.36 |
| B calibrator | 27 | 5.51 | 0.58 | 6.00 | 4.47 |
| C calibrator | 27 | 5.16 | 0.63 | 6.70 | 4.32 |

TABLE 3-continued

Mean, standard deviation, minimum, maximum and number of samples of the absorbance measurement of GALT-analyte for different sample types.

| Sample | n | Mean | STD | Max | Min |
|---|---|---|---|---|---|
| D calibrator | 27 | 5.10 | 0.64 | 6.00 | 4.27 |
| E calibrator | 27 | 5.24 | 0.59 | 6.60 | 4.48 |
| F calibrator | 27 | 5.44 | 0.65 | 6.70 | 4.43 |
| N control | 27 | 5.47 | 0.51 | 6.13 | 4.69 |
| AbN control | 27 | 5.07 | 0.56 | 6.00 | 4.35 |
| Hkr 0.3 | 27 | 2.96 | 0.38 | 3.86 | 2.31 |
| Hkr 0.3, disk removed | 9 | 2.31 | 0.19 | 2.53 | 2.03 |
| Hkr 0.4 | 27 | 3.73 | 0.23 | 4.19 | 3.35 |
| Hkr 0.4, disk removed | 9 | 3.04 | 0.12 | 3.19 | 2.85 |
| Hkr 0.5 | 27 | 4.76 | 0.57 | 6.00 | 4.05 |
| Hkr 0.6 | 27 | 5.39 | 0.62 | 6.30 | 4.47 |
| White disk | 27 | 0.46 | 0.16 | 0.87 | 0.22 |
| No disk | 27 | 0.08 | 0.02 | 0.11 | 0.06 |
| Empty well | 27 | 0.04 | 0.00 | 0.04 | 0.03 |

The invention claimed is:

1. A method for detecting elution of a sample from a sample substrate to incubation buffer contained in a sample well comprising:
    measuring light absorption of the contents of the sample well at a predefined wavelength or wavelength range, and
    determining, based on the absorption measurement, the degree of elution of the sample, wherein the sample substrate is present in the sample well during said measurement and a wavelength or wavelength range is used which is absorbed by at least one elutable component of the sample but transmitted by the sample substrate, and
wherein absorbance of the at least one elutable component of the sample is at least 3 times higher than the absorbance of the sample substrate at said wavelength or wavelength range.

2. The method according to claim 1, wherein the sample is a blood sample and the elutable component is haemoglobin.

3. The method according to claim 1, wherein the wavelength is approximately 420 nm or the wavelength range comprises the wavelength of 420 nm.

4. The method according to claim 1, wherein the sample substrate is a fibrous substrate.

5. The method according to claim 1, wherein the method is performed automatically in parallel or successive fashion for a plurality of sample wells in an optical sample measurement apparatus.

6. The method according to claim 1, wherein said light absorption measurement comprises
    directing light through the sample well at said selected wavelength or wavelength range from above the sample well, and
    detecting light transmitted from below the sample well.

* * * * *